United States Patent [19]

Lange

[11] 4,216,381
[45] Aug. 5, 1980

[54] STRUCTURE FOR EMISSION TOMOGRAPHY SCINTILLATION CAMERA

[75] Inventor: Kai Lange, Vedbaek, Denmark

[73] Assignee: General Electric Company, Milwaukee, Wis.

[21] Appl. No.: 37,661

[22] Filed: May 10, 1979

[51] Int. Cl.² .............................................. G01T 1/20
[52] U.S. Cl. .................................. 250/363 S; 250/521
[58] Field of Search ................ 250/363 S, 445 T, 505, 250/522, 523, 521

[56] References Cited

U.S. PATENT DOCUMENTS

| 3,735,132 | 5/1973 | Carugati et al. | 250/363 S |
| 3,983,399 | 9/1976 | Cox, Jr. et al. | 250/363 S |
| 4,057,726 | 11/1977 | Jaszczak | 250/363 S |
| 4,057,727 | 11/1977 | Muehllehner et al. | 250/363 S |
| 4,066,902 | 1/1978 | Lemay | 250/363 S |

Primary Examiner—Davis L. Willis
Attorney, Agent, or Firm—Dana F. Bigelow

[57] ABSTRACT

A supporting structure allows a conventional, counterbalanced scintillation camera to be adapted for emission tomography analysis by rotating a detector in a circular orbit about a patient. The structure includes a base having a pair of upright stanchions supporting an upright circular frame which has a central, longitudinal axis. The upright circular frame comprises an outer circular ring and a concentric inner circular ring adapted for concentric relative rotation. An elongated frame pivotally supports a detector at one end and has a counterweight at the other end is tiltably mounted within the inner circular ring of the circular frame. The structure includes a drive system for rotating the elongated frame within the circular frame whereby the detector orbits the patient to receive emission data.

7 Claims, 2 Drawing Figures

STRUCTURE FOR EMISSION TOMOGRAPHY SCINTILLATION CAMERA

BACKGROUND OF THE INVENTION

The invention relates generally to imaging devices for detecting radiation distribution by a scintillation camera. The invention relates particularly to a stand for adapting a conventional scintillation camera for emission computed axial tomography analysis of a patient.

In a scintillation camera adapted for trans-axial tomographic scanning, a scintillation detector precesses in an orbit about a patient having an axis of precession corresponding to the cranial-caudal axis of the patient. The scintillation detector head employs an array of photodetectors viewing overlapping portions of a scintillation crystal which is formed in the shape of a disk. Radiation impinging upon the crystal, which is typically formed of sodium iodide, causes flashes of light to be emitted which are detected by photomultiplier tubes viewing the area of emission. The photomultiplier tubes generate electrical signals proportional to the magnitude of the light intensity received. These signals are matrixed together to provide positional information, thereby locating the point of origin of the scintillation in the plane of the crystal. If a collimator is interposed between the radiation source and the detector crystal, the location of the scintillation will correspond to the point of origin in the patient of the incident gamma ray causing the scintillation. This point is then depicted in a two-dimensional matrix. This brief description of the operation of a scintillation camera is adequate for purposes of this invention, as the basic principles are explained at length in U.S. Pat. No. 3,011,057.

In trans-axial tomographic scanning, a radiation detector is moved in an orbit about a subject of interest rotating to face the subject of interest at all times. Typically, the subject of interest is a human patient and the orbit in which the radiation detector moves is a circular orbit in which the axis of the circle about which the detector precesses is referred to as the cranial-caudal axis. The scintillation detector is always tangent to this circle.

In trans-axial tomographic scanning a single precession of a scintillation camera detector about the patient produces an image showing the radioactive distribution in a plurality of section imaging planes, which are transverse planes that are mutually parallel and usually perpendicular to the cranial-caudal axis. Gamma rays eminating both from within and from without these planes are detected. Detected radiation producing scintillations in the crystal detector is associated by computational and storage means with the nearest section imaging plane. The motion of the scintillation camera detector about the cranial-caudal axis is digitized and represented in electronic form in a computation means, such as a small computer. Using an appropriate algorithm, the computer concurrently determines the distribution of radioactive events within a plurality of parallel section imaging planes typically having a thickness of about 2 centimeters. The computed radioactive distribution is displayed on a visual image display device. Precession continues for imaging in the section imaging plane until the scintillation detector has moved 360° about the cranial-caudal axis. In theory, a precession through only 180° would be practical, but precession through 360° is performed to minimize internal attenuation effects insofar as is possible. While precession of the detector is preferably, a continuous advancement through the detector orbit data registration within a particular imaging frame is performed in discrete counting intervals which are initiated and terminated in stepwise increments.

A particular problem associated with emission computed axial tomography is that the orbiting structure and mechanism are usually quite elaborate and expensive, and also require unique detector heads. Examples of such structures are shown in U.S. Pat. Nos. 4,057,726 and 4,057,727. The use of such structures is also limited to the mode of axial tomography analysis and the structure can not be efficiently used for conventional stationary radiation distribution analysis of a patient.

Accordingly, one object of the present invention is to provide a structure in which a conventional, counterbalanced scintillation camera can be used for emission tomography.

Another object of the present invention is to provide a structure in which a conventional, counterbalanced scintillation camera can be utilized for either emission tomography or conventional stationary radiation distribution analysis.

SUMMARY OF THE INVENTION

The invention is directed to a supporting structure for a scintillation camera. The supporting structure allows a conventional, counterbalanced scintillation camera to be adapted for emission tomography analysis by rotating the detector in a circular orbit about a patient. The structure includes a base having a pair of upright stanchions supporting an upright circular frame, which has a central, longitudinal axis. The upright circular frame comprises an outer circular ring and a concentric inner circular wing adapted for concentric relative rotation. An elongated frame pivotally supporting a detector at one end and having a counterweight at the other end is tiltably mounted within the inner circular ring of the circular frame. The elongated frame is mounted at the general lateral axis of balance of the frame and includes a means for tilting the elongated frame relative to the central longitudinal axis of the upright circular frame. The structure includes a drive system for rotating the elongated frame within the circular frame whereby the detector orbits the patient to receive emission data. The data is digitized and processed in electronic form. Using an appropriate algorithm, the computed radiographic distribution is constructed and is then displayed on a visual image display device.

BRIEF DESCRIPTION OF THE DRAWINGS

While the novel features of the invention are set forth with particularity in the appended claims, the invention will be better understood, along with other features thereof, from the following detailed description, taken in conjunction with the drawings, in which:

DESCRIPTION OF THE PREFERRED EMBODIMENT

Figure 1:
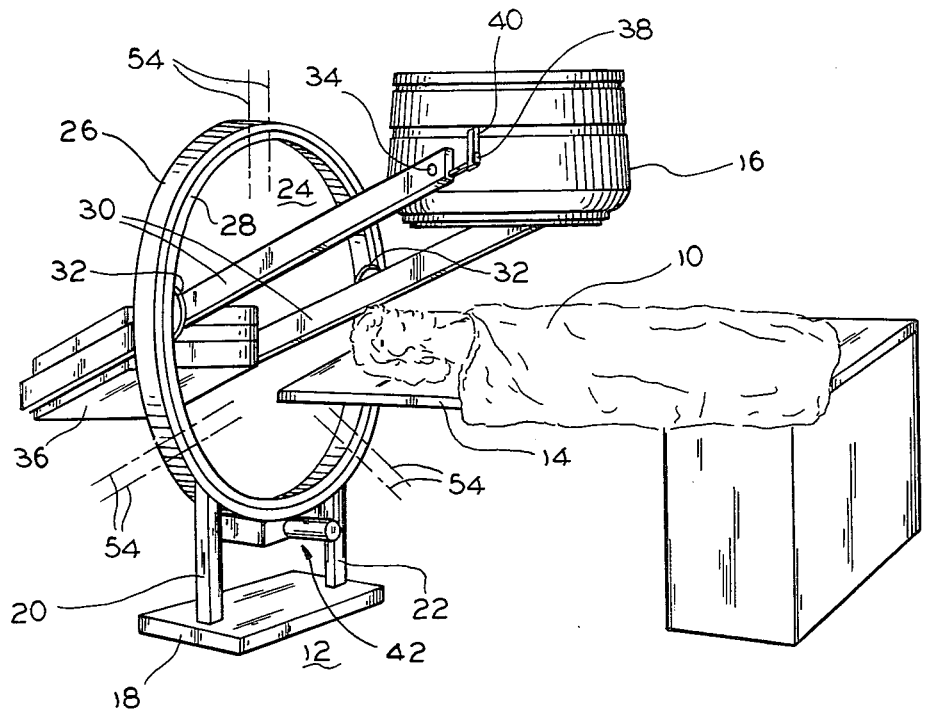
FIG. 1 is a perspective view of a patient undergoing analysis by a scintillation camera incorporating the present invention.

Referring first to FIG. 1, there is shown a patient 10 undergoing examination by an emission tomography camera system 12, while being supported by a cantilevered table 14. During this analysis, the patient 10 receives an internal dose of radiopharmaceutical compounds which emit gamma ray energy. The gamma ray energy is detected by a detector 16 for imaging internal portions of the patient. The detector 16 contains scintillation crystals, photomultiplier tubes, and lead shielding which perform in a well known manner to detect the precise location of the emissions from the patient.

In accordance with the present invention, a structure is provided for supporting the detector 16 and for rotating the detector in a circular orbit around the patient. The structure includes a base, 18, having upright stanchions 20 and 22 extending vertically therefrom and supporting an upright circular frame 24. The upright circular frame comprises an outer circular ring 26 and a concentric inner circular ring 28 adapted for concentric relative rotation. The inner circular ring supports an elongated frame 30 at trunions 32. The elongated frame 30 pivotally supports the detector head 16 at trunions 34 and has a counterweight 36 at the opposite end. The frame 30 is positioned generally at the lateral axis of balance between the detector head and the counterweight so that the detector head can be easily tilted to a desired position. Trunions 32 and 34 are each adapted with a releasable electromagnetic brake, which is controlled by an actuator 38 on handle 40. The actuator releases the brake and allows the detector head to be pivoted within trunions 34 and the frame 30 to be tilted within trunions 32 for the desired position relative to the patient 10. For emission tomography, it is desired to position the detector 16 as closely as possible to the patient without interferring with the patient. Trunions 32 and 34 include a graduated 360° index (not shown) to facilitate the positioning of the detector relative to the patient.

For emission tomography, the patient 10 is generally positioned along the central longitudinal axis of the circular frame 24. The detector 16 is carefully positioned so that it is close to the patient and is tangent to the orbital path without interferring with the patient or the table. A drive system 42 provides the means for rotating the elongated frame 30 within circular frame 24 by rotating the inner ring 28 relative to the outer ring 26. The drive system is carefully controlled so that the detector will be advanced an incremental step while the emission data is being accumulated. As a typical example, the detector is advanced through 128 evenly spaced increments during a 360° orbit of the patient. In other examples, the detector could slowly rotate continuously about the patient or could be advanced at any number of specific positions for a specific analysis. The angular position of the detector is encoded to correlate with the emission data, as will be described later. The detected radiation producing scintillations in the detector is associated by well known computational and storage means (not shown) with the nearest section imaging plane. The encoded position of the detector is also digitized and processed in the computational and storage means. An appropriate and well known algorithm is used to reconstruct the data for display on a conventional visual image display device (not shown).

Figure 2:
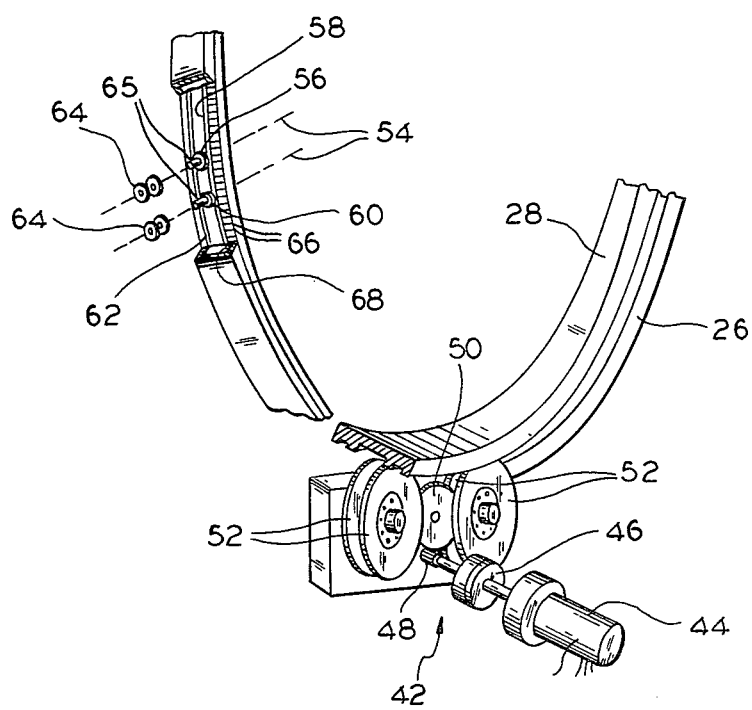
FIG. 2 is a partially cut-away perspective view showing the bearing support and drive system for the structure shown in FIG. 1.

Referring also to FIG. 2, there is shown some details of the drive system and the bearing support for the circular frame. A suitable drive system is provided by a motor 44 operating through an electromagnetic clutch 46, controlling a drive gear 48. Drive gear 48 engages a spur gear 50 which actuates four drive rollers 52. The drive rollers 52 engage the outer periphery of inner circular ring 28 to rotate the detector around the patient.

The inner circular ring 28 is stabilized within the outer ring 26 by 3 sets of stabilizing rollers indicated by roller axes 54 evenly spaced at 120° increments around the circular frame. A guide roller 56 is positioned to engage a forward circumferential flange 58 on the inner circular ring 28. Similarly, a guide roller 60 is positioned to engage a rear circumferential flange 62 on the innner ring. Eccentric rollers 64 are mounted on shafts 65 and are similarly positioned to engage circumferential flanges on the inner surface of outer ring 26 to precisely stabilize the concentric rings of the upright circular frame.

A suitable means for encoding the relative rotational position of the detector in correlation with the emission data is shown in FIG. 2. Inner circular ring 28 includes a continuous series of alternate light and dark portions 66 on the outer periphery. The outer ring 26 includes photodiodes 68 adapted to respond to the light and dark portions of the inner ring which pass the photodiodes and thereby encode the position of the detector by conventional circuitry to the control system. The encoded position can be used for correlating the emission data and for controlling the advancement of the drive system 42.

A primary advantage of the structure is the efficient and inexpensive adaptation of the conventional scintillation camera into an emission tomography camera. An additional advantage is that the structure allows the detector to also be positioned for conventional emission analysis for efficient utilization of the device. For conventional emission analysis, the control system deactivates the drive system and the data is compiled and displayed in the conventional manner. To position the detector 16 over the patient, the actuator 38 is pressed which releases the electromagnetic brakes in trunions 32, 34, and in the electromagnetic clutch 46. The detector head 16 is then free to be positioned and the release of the actuator will fix the detector in the desired position.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A structure for a scintillation camera having a detector adapted for emission tomography analysis of a patient, comprising:
   a base;
   an upright stanchion mounted on said base;
   an upright circular frame, having a central longitudinal axis, mounted on said stanchion;
   an elongated frame pivotally supporting the detector at one end and having a counterweight at the other end, having means for mounting the lateral axis of balance of said elongated frame tiltably within said circular frame;
   means for tilting said elongated frame relative to the central longitudinal axis; and
   means for rotating said elongated frame within said circular frame, whereby the detector orbits the patient to receive emission data.

2. The structure, as recited in claim 1, wherein said upright circular frame comprises an outer circular ring and a concentric inner circular ring adapted for concentric relative rotation.

3. The structure, as recited in claim 2, wherein said mounting means includes trunion connectings to said inner circular ring for rotation therewith.

4. The structure, as recited in claim 3, wherein said trunion connections include releasable brakes so that the angular tilt of the elongated frame can be locked at desired angular positions.

5. The structure, as recited in claim 2, wherein said inner circular ring includes a continuous series of light and dark portions around the outer periphery thereof, and said outer circular ring includes a fixed photodiode adapted to respond to the light and dark portions of said inner circular ring which pass the photodiode, thereby encoding the position of the detector.

6. The structure, as recited in claim 2, wherein the rotating means comprises:

a drive motor mounted to said outer circular ring and having at least one drive gear; and said inner circular ring adapted to engage the drive gear of said drive motor.

7. The structure, as recited in claim 1, wherein said circular frame includes means for encoding the relative rotational position of the detector in correlation with emission data received by the detector.

* * * * *

REEXAMINATION CERTIFICATE (924th)
United States Patent [19]
Lange

[11] B1 4,216,381
[45] Certificate Issued  Sep. 27, 1988

[54] STRUCTURE FOR EMISSION TOMOGRAPHY SCINTILLATION CAMERA

[75] Inventor: Kai Lange, Vedbaek, Denmark

[73] Assignee: General Electric Company, Milwaukee, Wis.

Reexamination Request:
No. 90/001,358, Oct. 15, 1987

Reexamination Certificate for:
Patent No.: 4,216,381
Issued: Aug. 5, 1980
Appl. No.: 37,661
Filed: May 10, 1979

[51] Int. Cl.⁴ .................................................. G01T 1/20
[52] U.S. Cl. ................................................. 250/363 S
[58] Field of Search ............... 250/363 SR, 363 SB, 250/363 SC, 363 SF; 378/177, 208, 209

[56] References Cited
U.S. PATENT DOCUMENTS

| | | | |
|---|---|---|---|
| 2,364,363 | 12/1944 | Howell | 95/86 |
| 3,549,885 | 12/1970 | Andersson | 250/61.5 |
| 3,735,132 | 5/1973 | Carugati et al. | 250/363 S |
| 3,756,549 | 9/1973 | Lange | 248/123 |
| 3,983,399 | 9/1976 | Cox, Jr. et al. | 250/363 S |
| 4,047,037 | 9/1977 | Schlosser et al. | 250/370 |
| 4,057,726 | 11/1977 | Jaszczak | 250/363 S |
| 4,057,727 | 11/1977 | Muehllehner et al. | 250/363 S |
| 4,066,902 | 1/1978 | Lemay | 250/363 S |
| 4,220,861 | 9/1980 | Colombo et al. | 250/363 S |

FOREIGN PATENT DOCUMENTS

925421  2/1954  Fed. Rep. of Germany.

*Primary Examiner*—Janice A. Howell

[57] ABSTRACT

A supporting structure allows a conventional, counterbalanced scintillation camera to be adapted for emission tomography analysis by rotating a detector in a circular orbit about a patient. The structure includes a base having a pair of upright stanchions supporting an upright circular frame which has a central, longitudinal axis. The upright circular frame comprises an outer circular ring and a concentric inner circular ring adapted for concentric relative rotation. An elongated frame pivotally supports a detector at one end and has a counterweight at the other end is tiltably mounted within the inner circular ring of the circular frame. The structure includes a drive system for rotating the elongated frame within the circular frame whereby the detector orbits the patient to receive emission data.

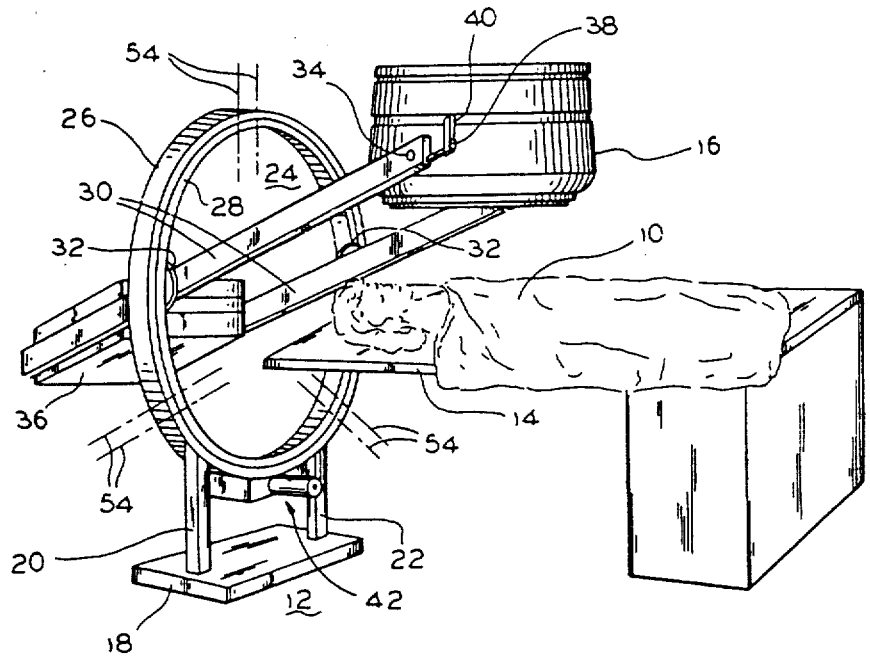

B1 4,216,381

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–7 is confirmed.

New claims 8 and 9 are added and determined to be patentable.

*8. A structure for a scintillation camera having a detector adapted for emission tomography analysis of a patient, comprising:*

*a base;*

*an upright stanchion mounted on said base;*

*an upright circular frame, having a central longitudinal axis, mounted on said stanchion, said frame defining a central aperture having a size sufficient to receive said patient;*

*an elongated frame pivotally supporting the detector at one end and having a counterweight at the other end, having means for mounting the lateral axis of balance of said elongated frame tiltably within said circular frame;*

*means for tilting said elongated frame relative to the central longitudinal axis; and*

*means for rotating said elongated frame within said circular frame, whereby the detector orbits the patient to receive emission data.*

*9. A structure for a scintillation camera having a detector adapted for emission tomography analysis of a patient, comprising:*

*a base;*

*an upright stanchion mounted on said base;*

*an upright circular frame, having a central longitudinal axis, mounted on said stanchion;*

*an elongated frame pivotally supporting the detector at one end and having a counterweight at the other end, having means for mounting the lateral axis of balance of said elongated frame tiltably within said circular frame, said elongated frame including a pair of side members defining a space, said space having a size sufficient to receive said patient;*

*means for tilting said elongated frame relative to the central longitudinal axis; and*

*means for rotating said elongated frame within said circular frame, whereby the detector orbits the patient to receive emission data.*

* * * * *